(12) United States Patent
Chapman, III

(10) Patent No.: US 9,869,665 B2
(45) Date of Patent: Jan. 16, 2018

(54) GENERATOR PREDICTIVE ENGINE OIL LIFE ALGORITHM

(71) Applicant: Kohler Co., Kohler, WI (US)

(72) Inventor: William F. Chapman, III, Grafton, WI (US)

(73) Assignee: Kohler, Co., Kohler, WI (US)

( * ) Notice: Subject to any disclaimer, the term of this patent is extended or adjusted under 35 U.S.C. 154(b) by 696 days.

(21) Appl. No.: 14/284,946

(22) Filed: May 22, 2014

(65) Prior Publication Data

US 2015/0338386 A1 Nov. 26, 2015

(51) Int. Cl.
*G01N 33/28* (2006.01)
*F01M 11/10* (2006.01)

(52) U.S. Cl.
CPC ......... *G01N 33/2888* (2013.01); *F01M 11/10* (2013.01); *F01M 2011/14* (2013.01)

(58) Field of Classification Search
CPC ............... F01M 11/10; F01M 2011/14; G01N 33/2888; F02D 41/021
USPC ....... 702/23, 50, 52; 73/53.01, 53.05, 61.45, 73/114.55; 701/29.51, 29.5, 29.1
See application file for complete search history.

(56) References Cited

U.S. PATENT DOCUMENTS

| | | | |
|---|---|---|---|
| 4,796,204 A | 1/1989 | Inoue | |
| 4,847,768 A | 7/1989 | Schwartz et al. | |
| 5,732,676 A | 3/1998 | Weisman et al. | |
| 5,969,601 A | 10/1999 | Sato et al. | |
| 5,987,976 A | 11/1999 | Sarangapani | |
| 6,037,864 A | 3/2000 | Sem et al. | |
| 6,253,601 B1 | 7/2001 | Wang et al. | |
| 6,732,572 B1 | 5/2004 | Pickert et al. | |
| 6,741,938 B2 | 5/2004 | Berndorfer | |
| 6,920,779 B2 | 7/2005 | Carlstrom et al. | |
| 7,370,514 B2 | 5/2008 | Halalay et al. | |
| 8,340,928 B2 | 12/2012 | Sun | |
| 8,464,576 B2 | 6/2013 | Okuyama et al. | |
| 2004/0099050 A1* | 5/2004 | Matsiev ................ | F02D 41/021 73/61.45 |
| 2009/0234533 A1 | 9/2009 | Trinkner | |
| 2012/0303230 A1 | 11/2012 | Qiao et al. | |
| 2013/0068003 A1 | 3/2013 | Kumar et al. | |
| 2013/0131912 A1 | 5/2013 | Chen et al. | |

(Continued)

FOREIGN PATENT DOCUMENTS

| | | |
|---|---|---|
| WO | WO2013014202 | 1/2013 |
| WO | WO2013068022 | 5/2013 |

OTHER PUBLICATIONS

Dan Peterson, Your Oil Life Monitoring System is Not an on-board Chemist, Oct. 2011, AMS Oil Magazine.

(Continued)

*Primary Examiner* — John H Le
(74) *Attorney, Agent, or Firm* — Lempia Summerfield Katz LLC

(57) ABSTRACT

A system including one or more generators predicts engine oil life. Generator data is received or generated by a controller. The generator data describes the operation of the generator including a load placed on the generator. Engine data may also be received or generated by the controller describing an engine coupled to the generator. The controller calculates an estimated oil life based at least on the generator data and/or the engine data.

18 Claims, 8 Drawing Sheets

(56) References Cited

U.S. PATENT DOCUMENTS

2013/0255603 A1 10/2013 Pursifull et al.
2013/0297142 A1 11/2013 Geng et al.

OTHER PUBLICATIONS

Honda Maintenance, Mar. 6, 2014, Honda Cars of Corona.
Kohler Power Systems, Technical Information Bulletin, Mar. 6, 2014.
European Search Report for related European Application No. 15168667.2 dated Oct. 9, 2015.

* cited by examiner

GENERATOR PREDICTIVE ENGINE OIL LIFE ALGORITHM

TECHNICAL FIELD

This disclosure relates in general to predicting engine oil life in a generator, or more particularly, to an algorithm for predicting engine oil life in a generator based on operation of the generator.

BACKGROUND

Engine oil lubricates the moving parts of an engine and decreases friction and heat between the parts of the engine. Oil is made from petroleum based compounds or synthetic compounds. In either case, heat breaks down the oil. Broken down oil may tend to get watery or gummy. Accordingly, engine oil should be replaced periodically.

Replacement of the engine oil is one of the most important types of maintenance to be performed on the engine. Some engine manuals (e.g., lawnmowers or other small engines) may instruct the user to replace the engine oil every year or every season. Automotive manufacturers may recommend that engine oil be changed based on a usage distance (e.g., every 3,000 miles) or based on a period of time (e.g., every 3 months), whichever comes first.

However, the life of engine oil is not as simple as a travel distance or a usage time. Some applications of an engine, such as power generator systems, may operate in sporadic patterns that are not easily predicted by existing algorithms.

BRIEF DESCRIPTION OF THE DRAWINGS

Exemplary implementations are described herein with reference to the following drawings.

DETAILED DESCRIPTION

Figure 1:
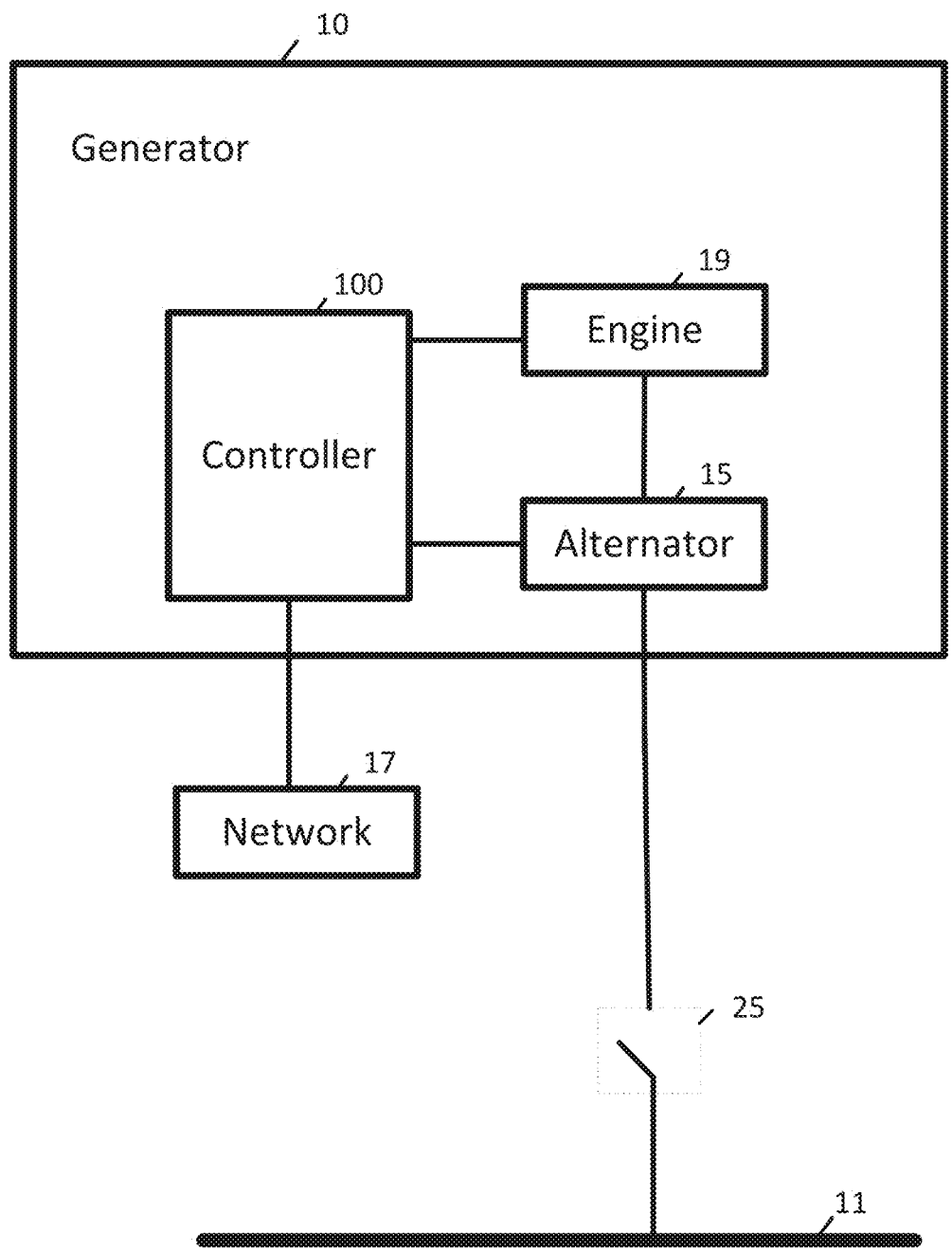
FIG. 1 illustrates an example generator including an algorithm for predicting oil life.

An engine-generator set, which may be referred to as a generator or a genset, may include an engine and an alternator or another device for generating electrical energy or power. The engine may combust a fuel (e.g., gasoline, diesel, gaseous fuel) to move pistons that reciprocate within cylinders to move connecting rods that rotate a crankshaft. A sump surrounds the crank shaft and acts as a reservoir to collect and store engine oil. The engine oil lubricates the moving parts.

The engine rotates the alternator to provide power to a load through a power bus. The power bus, which may be referred to as a generator bus or common bus, may be connected to multiple generators. A generator communication network may include one or more transfer switches, one or more generator controllers, and one or more centralized controllers. The generator controllers manage the operation of the generators including output levels, engine speeds, and synchronization timing. The transfer switches or centralized controllers may manage switching the generators to and from a load and may also coordinate operations among generator controllers such as load sharing and load shedding.

In automotive applications, engines are often run very frequently for relatively short time periods. Typically, a vehicle is driven to and from work or school nearly every day. When the automobile is in use, the same type of use is repeated. For example, driving at 55 miles per hour. The life of the oil can be judged through broad estimates (e.g., change the oil every 3,000 miles or 3 months).

Generator applications, on the other hand, may have very different usage patterns. A generator may be installed, tested, and then remain unused for weeks, months, or years. In other example, a generator may be run constantly for a few hours or days, and then not see additional service for extended periods of time. Some engine manufacturers provide customers and distributors with recommended service intervals for engine oil changes every one year or 100 hours of operation. However, based on ambient conditions, consecutive operating hours, engine speed, and engine load, these recommended service intervals can become invalid.

For example, a one year engine oil interval may be acceptable when the generator exercising occurs on a weekly basis. However, when an electrical outage occurs, a generator may run 24 to 48 hours continuously. During this time, the engine is under extreme stress providing electrical power to the building. This may be especially true for smaller generators that are air cooled in extreme temperature environments. After these long continuous generator operation periods, the engine oil may have degraded at a faster pace. If the owner or distributor has not properly tracked the generator rung time, continuing to operate at extreme conditions could result in excessive engine wear and damage.

Accordingly, the one-size-fits all estimation of changes the oil after a predetermined number of engine hours or a predetermined amount of total time may not accurately estimate oil life for generator applications. In addition, typical customers do not accurately track hours of operation or remember to change the oil once a year.

The following examples include an oil life prediction algorithm that uses data available by the generator to estimate the engine oil life remaining for generator systems. The generator controller or other connected controller may execute the prediction algorithm to predict when the engine oil life has degraded. The customer may be sent an automatic message to have their generator serviced. Customer units are properly serviced based on individual usage conditions rather than one-size-fits all estimation.

FIG. 1 illustrates an example generator 10 including an algorithm for predicting oil life. The generator 10 includes an alternator 15 driven by an engine 19 and a controller 100. The generator 10 is stationary and produces an alternating current (AC) output suitable to provide electrical power (e.g., to a home, building, boat or other system). The controller 100 is in communication with the engine 19 and the alternator 15. The controller 100 may be in communication with a network 17. The network 17 may allow the controller 100 to communicate with other generator controllers, with the internet, or with a mobile device. The alternator 15 may include a rotor and a stator. The stator may include output windings, and the rotor may include field windings.

The generators 101*a-b* may also include a fuel supply, a speed governor, a cooling system, an exhaust system, a lubrication system, and a starter. Additional, different, or fewer components may be included. Example types of generators include towable generators, portable generators, marine generators, industrial generators, residential generators or other standby generators. The generators may be semi-permanent or permanent.

The controller 100 may generate and send commands to the engine 19 and to the alternator 15. The controller 100 may instruct the engine 19 to start. The controller 100 may instruct the engine 19 to run at a particular speed or frequency or instruct the engine 19 to make incremental adjustments in speed or frequency. The controller 100 may instruct the alternator 15 to provide a particular field current to the field windings or output a particular voltage or instruct the alternator 15 to make incremental adjustments in field current, which defines or affects the output of the alternator 15.

The commands or instructions for the controller 100 may be generator data for the operation of the generator or adjustment of the output of the generator. In other words, the actual operation of the generator 10 may be inferred from the instructions sent by the controller 100. If the controller 100 instructs the alternator 15 to output 50% of the rated output, it is assumed that this level is achieved. In another example, the controller 100 may receive data for the operation of the generator based on measured data collected from one or more sensors. The sensors may include any combination of a voltage sensor, a current sensor, or another electrical sensor.

The commands or instructions for the controller 100 may be engine data for the operation of the engine 19. In other words, the actual operation of the engine 19 may be inferred from the instructions sent by the controller 100. If the controller 100 instructs the engine 19 to output 50% of the rated output, it may be assumed that this level is achieved. In another example, the controller 100 may receive data for the operation of the generator 10 based on measured data collected from one or more sensors. The sensors may measure movement of the engine 19 abased on any or any combination of a tachometer, a torque sensor, a deflection sensor, a dynamometer, a positional sensor, or a revolution sensor. The sensors may include a temperature sensor to measure engine oil temperature. The temperature sensor may be mounted in or coupled to the sump of the engine 19.

The controller 100 calculates an estimated oil life based at least on the generator data or the engine data. The estimated oil life may be a function generator load from the alternator 15 and engine speed from the engine 19. The estimated oil life may be a function of any or any combination of generator load, engine speed, oil temperature, and operation time.

The generator 10, alternator 15, and/or engine 19 may be securely and physically connected to a particular location. In one example, the physical connection is a fuel supply (e.g., a gas line from a house or an external tank). In another example, the physical connection may be bolts or other securing device that secure the generator 10. In one example, the generator 10 is portable or towable but the physical connections (e.g., gas line or securing device) is disconnected before the generator 10 is moved and reconnected at a new location.

The network 17 may allow the controller 100 to communicate with other generator controllers, with the internet, or with a mobile device using one or more of physical cables or wireless signals. The wireless signals may be any combination of the techniques known as Bluetooth, the techniques known as wireless or Wi-Fi, cellular communication, microwave communication, or another form of communication.

The alternator 15 may be an electromechanical device. The alternator 15 may include a rotating magnetic field and a stationary armature, a rotating armature with a stationary magnetic field, or a linear alternator. The engine 19 may be powered by gasoline, diesel fuel, or gaseous fuel. The gaseous fuel may be liquefied petroleum gas (LPG), hydrogen gas, natural gas, biogas, or another gas. The LPG may be or include primarily butane, primarily propane, or a mixture of hydrocarbon gases. The hydrogen gas may include hydrogen mixed with air or oxygen. The hydrogen gas may be mixed with another fuel when delivered to the engine. Natural gas (e.g., compressed natural gas (CNG)) may be a hydrocarbon gas mixture. Biogas may be a gas produced by the breakdown of organic material. Other variations are possible.

Figure 2:
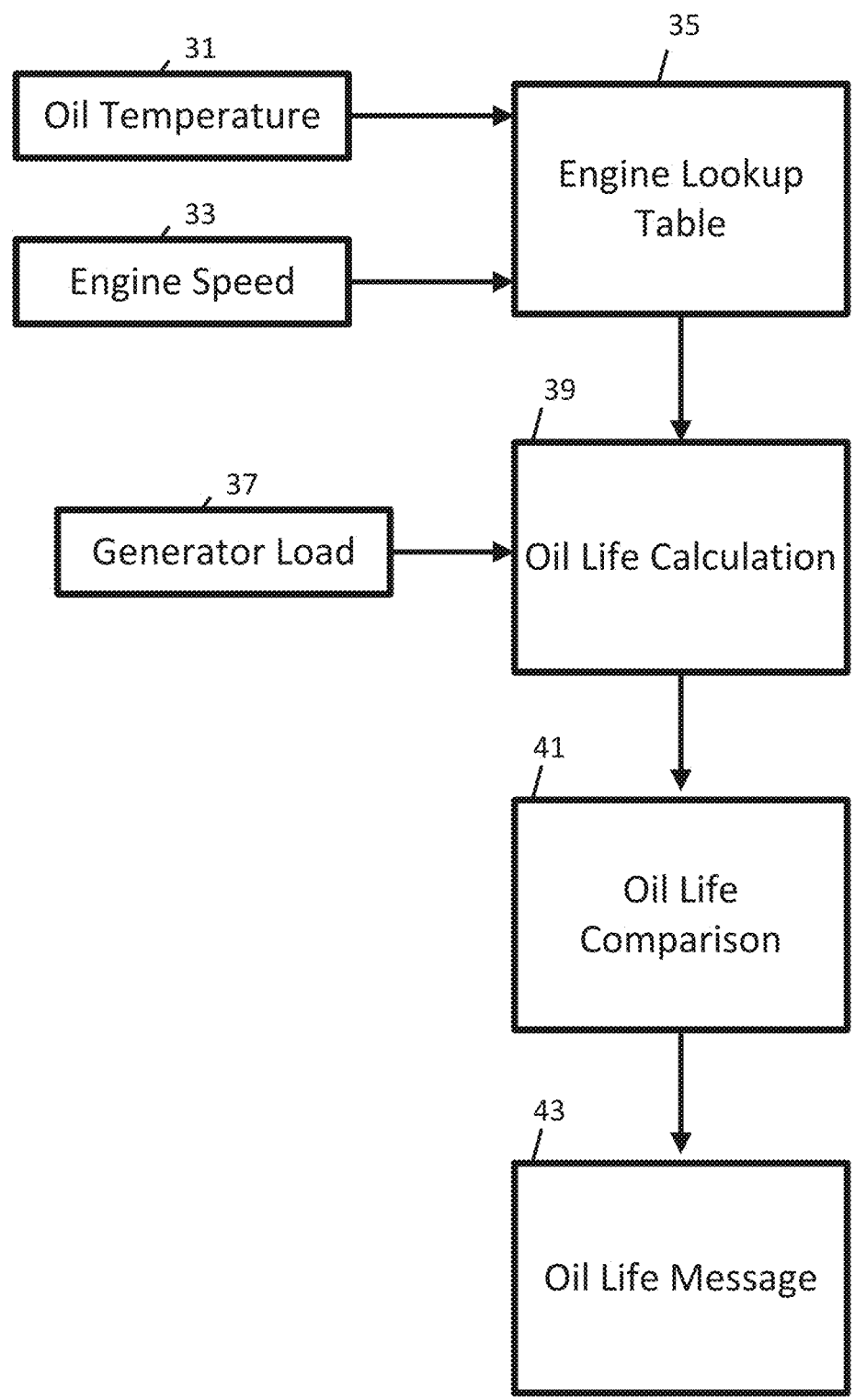
FIG. 2 illustrates an example algorithm for predicting oil life.

FIG. 2 illustrates an example algorithm for predicting oil life. Example inputs to the algorithm include oil temperature 31, engine speed 33, and generator load 37. In additional, elapsed time may be an input to various stages of the algorithm for predicting oil life. In addition, a reset signal may be an input to the algorithm for predicting oil life. The algorithm may include additional, different, or fewer states. Outputs from the algorithm may include an oil life estimation or an oil life message.

At stage 35, an engine lookup table combines the oil temperature 31 and the engine speed 33 to generate an engine factor. The lookup table may be generalized across all engine types. In another example, the look up table may include sections for different engine types, or independent tables for different engine types. The different engine types may be defined according to manufacturer, fuel type, model number, or rated output levels. The lookup table may be derived over time for a particular engine or a particular type of engine. Under extreme engine speeds and oil temperatures, the degradation of the oil increases and this oil life reduction increases at a faster rate. Operating at high engine speeds and/or high temperatures may cause oil molecules to be broken into smaller molecular chains reducing the effectiveness of the oil. The look up table may be created based on empirical data from running various engines at various loads and temperature points with interpolation across the operating range. The engine factor as a function of oil temperature 31 and the engine speed 33 may be determined every predetermined period (e.g., 100 milliseconds, 1 second, 1 minute, or another time period).

At stage 39, an oil life calculation determines an estimated oil life based on the engine factor output from stage 35 and a generator load 37. The generator load 37 may be a function of time. The oil life calculation may be a linear relationship that relates generator load 37 over a time period to calculate the estimated oil life.

Figure 3:
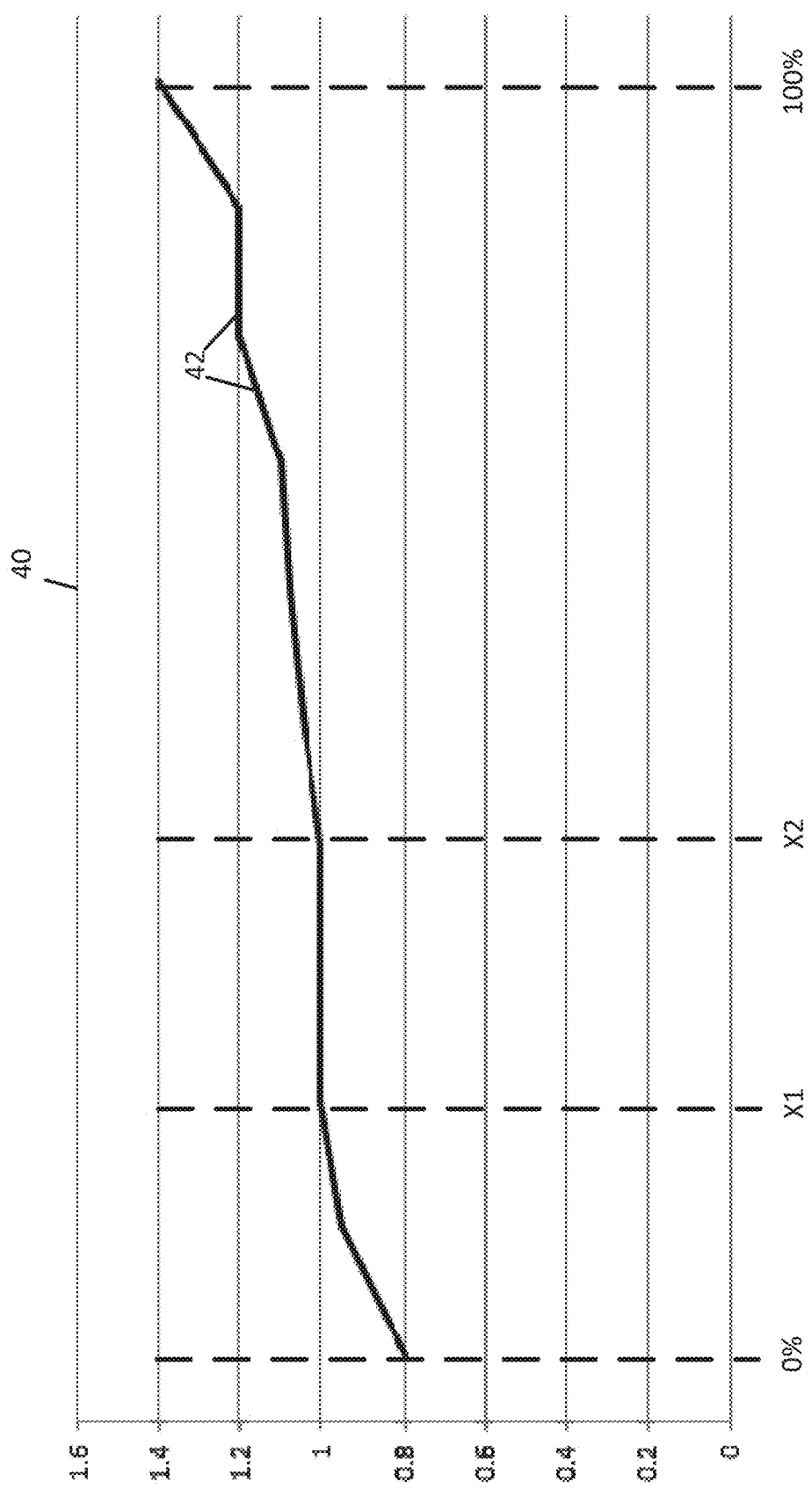
FIG. 3 illustrates an example relationship for generator load and oil life.

The oil life calculation may calculate a load factor based on the generator load 37. FIG. 3 illustrates an example chart 40 for the relationship between generator load and the load factor. The load factor may be based on a ratio of the actual or measured load to the maximum load per unit time for the generator. Data for the load factor may be collected, calculated, or aggregated for various engine-alternator combinations at varying loads. The horizontal axis of chart 40 may be the ratio of actual load to maximum load, or the percentage of rated output for the generator. The ratio may be a value between 0 to 1 or a percentage value. The vertical axis represents the load factor.

FIG. 3 illustrates three ranges for the load factor. A first range lower than X1, a second range between ratio X1 and X2, a third range greater than X3. Examples for {X1 and X2} include {20% and 40%} or {30% and 60%}. At the first range, the load factor may be below 1 at low alternator load since the load on the engine is minimal. At nominal loads or average loads, between, for example, X2 and X3 the load factor may be 1 and does not increase or decrease the oil life loss calculated by engine temperature and engine speed. However, at high loads greater than X2 the load factor will be greater than 1. This ratio may increase the loss of engine oil life under high load conditions.

The load factor for each of the ranges shown in FIG. 3 or additional ranges may be defined according to a linear function or a higher order relationship dependent on load. The relationship may be defined piecewise intervals within each range, as shown by sub-ranges 42. Thus, multiple linear relationships may be applied between X1 and X2 in FIG. 3.

The estimated oil life from stage 35 may be multiplied by the load factor to calculate an updated oil life. The multiplication may take place in discrete time intervals. For example, every 1 second, the current estimated oil life from stage 35 is multiplied by the load factor from stage 39. Rather than discrete time intervals, the calculation may be continuous. Stage 39 may include a feedback loop and repeat over the sequence of time intervals to repeatedly calculate the updated oil life.

At stage 41, the resulting updated oil life value may be compared to a threshold oil life. In one example, the threshold oil life is selected based on the type of oil. Example types of oil include synthetic oil versus conventional oil. The type of oil may be defined by any combination of the weight or thickness of the oil. The type of oil may be defined by viscosity grade.

The resulting updated oil life value may be compared to a maximum value. The maximum value may be a maximum possible oil life (e.g., 100 hours, 3 months). When the calculated updated oil life would extend past the maximum value, the updated oil life is reduced to the maximum value. Thus, the final estimated oil life is set to the maximum value when the estimated oil life exceeds the maximum value.

At stage 43, an oil life message may be generated based on the comparison to the threshold oil life. When updated oil life exceeds the oil life message no message may be generated or a normal operation message may be generated. When the updated oil life falls below the oil life message, a warning message may be generated. The warning message may be presented to the user either by a control panel on the generator or an external device. Multiple oil thresholds may be used. For example, when the updated oil life falls below a first threshold, a warning message is sent. When the updated oil life falls below a second threshold, a failure message may be sent or the generated may be shutdown.

Figure 4:
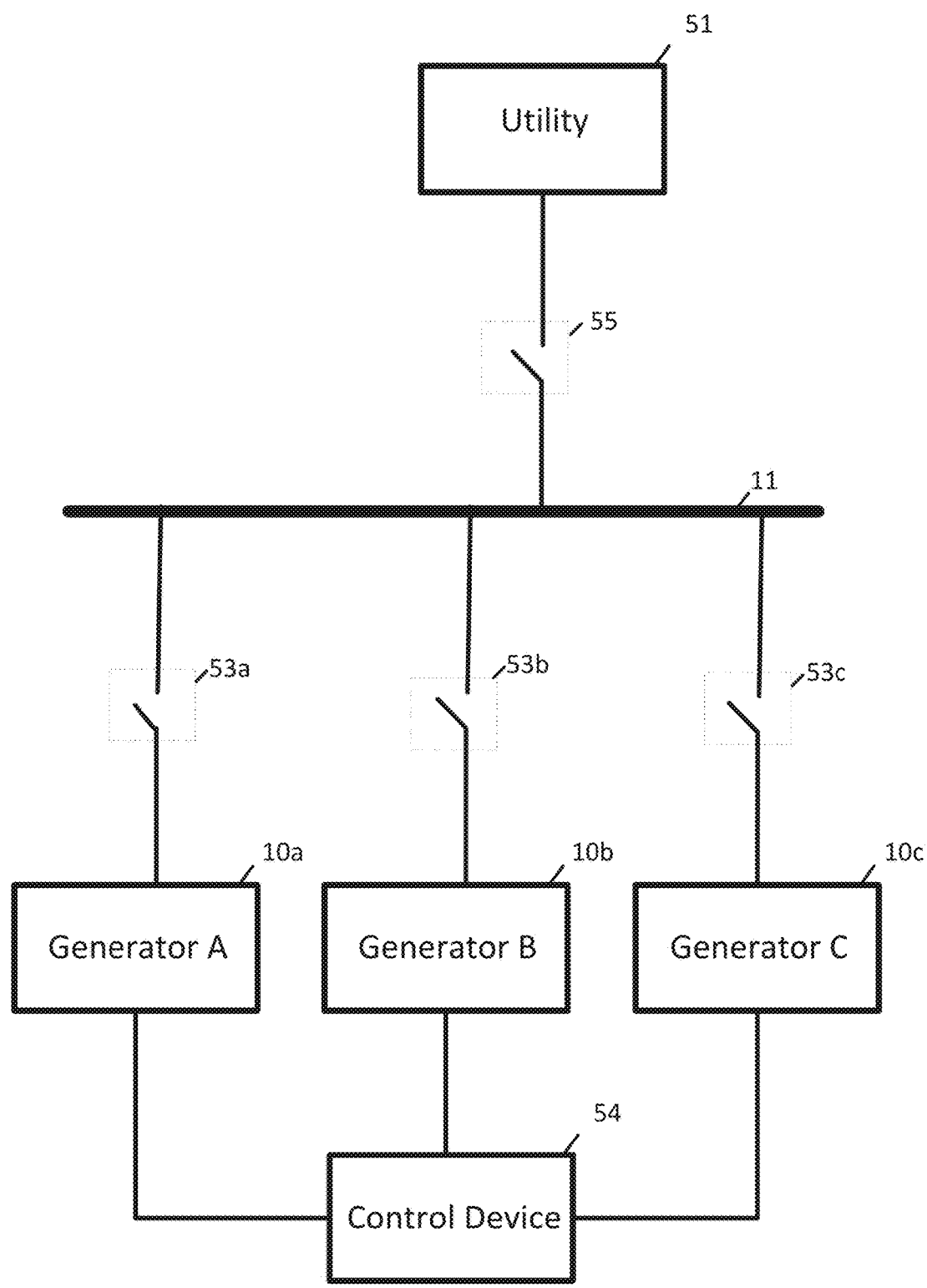
FIG. 4 illustrates an example system of generators and a central controller for predicting oil life.

FIG. 4 illustrates an example system of generators 10a-c and a central controller 54 for predicting oil life. The system of generators 10a-c are selectively coupled with generator bus 11 through circuit breakers 53a-c. The circuit breakers 53a-c may be switches controlled by the central controller 54. A utility system 51 (e.g., an electrical grid, a power company connection) may be selectively coupled with the generator bus 11 through circuit breaker 55. The circuit breakers 55 may be a switch controlled by the central controller 54. Additional, different, or fewer components may be included.

The central controller 54 may generate the engine lookup table for associating oil temperature, and the engine speeds to define an engine factor. For example, the central controller 54 may track the performance of an individual generator (e.g., generator 10a) or the system of generators 10a-c. To generate the lookup table the oil viscosity, oil temperature and the engine speed may be measured over time. The decay of the viscosity of the oil may be indicative of oil life. The viscosity of the oil may be detected by a viscosity sensor. The central controller 54 may track how much time elapses to reach a threshold viscosity based on oil temperature and engine speed combinations.

The system of generators 10a-c may be the same engine type (e.g., model, manufacturer, size, number of cylinders). The central controller 54 may generate a single engine lookup table for associating oil temperature and the engine speeds to define an engine factor.

The central controller 54 may generate the threshold oil life based on the performance of the generators 10a-c. The central controller 54 may receive data indicative of a type of oil. The type of oil may be received based on a user input from the control panel. The central controller 54 may monitor the viscosity of oil and calculate the threshold oil life based on when a particular type of oil passes a viscosity threshold.

The central controller 54 may exchange messages with individual controllers for generators 10a-c. The data communication may be RS 485, Modbus, universal serial bus (USB) or a derivative thereof. Modbus is a master and slave protocol defined by the Modbus Organization and available at www.modbus.org, which is incorporated by reference. The Modbus protocol may assign unique address to all devices connected to the bus 11. In some example, only a designated master device may send commands, including commands for other device to report data (e.g., status messages). In another example, any device may unilaterally send data using Modbus. A Modbus command or packet may include a destination address and a checksum. The destination address may indicate a unique address for a device in communication with the bus 11. The destination address may specify a classification of device. Example classifications include generator controllers, transfer switch controllers, and breaker controllers. A different alphanumeric code may correspond to each classification of device.

The messages exchanged between the central controller 54 and controllers of the individual generators 10a-c may include inbound communications and outbound communications with respect to the individual generators 10a-c. Inbound communication may include commands to start a generator, stop a generator, adjust an output of a generator, or adjust a speed of an engine of a generator. Outbound communications may include measured operating parameters of a generator or commands for other generators or a transfer switch.

The central controller 54 may determine the operation of the generator based on the inbound communications. For example, the central controller 54 may send a command to start a generator and in response, start a timer to measure the running time of the generator. Subsequently, the central controller 54 may send a command to stop the generator and in response, stop the timer. The elapsed time of the timer indicates the operation time of the generator.

The load on the generator during the elapsed timer may be set as the rated power output. Alternatively, the central controller 54 may send commands to adjust the output of the generator. The central controller 54 may calculate the total load on the generator based on the elapsed time and output levels described in the commands to adjust the output of the generator.

The central controller 54 may determine the operation of the generator based on the outbound communications or status messages. The status messages may include different types of information and be received from a variety of devices. Status messages may include connection information, operating parameters, measured data, or other information.

The connection information may include a connection status for various devices. The connection status may include data indicative of whether the device is connected to the bus 11. The connection information may include a switch setting for a circuit breaker. The switch stetting may indicate an ON status, an OFF status, an open status, or a closed status. The connection status may be received from controllers 100a and 100b or directly from the circuit breakers.

The operating parameters may include settings or outputs from the generators, the utility, or a transfer switch. The operating parameters may be inferred from settings (e.g., when the generator is set to output 120V, the operating parameter indicates 120V even though actual levels may vary). The settings may include a power setting, a voltage output setting, a frequency setting or another output setting. Alternatively, the operating parameters may include measured data collected from one or more sensors. The sensors may include any combination of a voltage sensor, a current sensor, a tachometer, a torque sensor, a deflection sensor, a dynamometer, a positional sensor, or a revolution sensor.

Any or all of the inbound or outbound communications may include an identifier that describes the sender. The identifier may include a code that is associated with the type of sending device (e.g., G for generator, S for transfer switch, or U for utility). The identifier may include a serial number of the sending device, a model number of the sending device, a rating of the sending device, or a network address of the sending device. The rating of the sending device may be a power rating (e.g., 20 kW, 40 kW, or another value), a voltage rating (e.g., 50 V, 120 V, 240 V, or another value), or an age rating (e.g., number of operating hours, model year, or another value).

The central controller 54 may control the loads on generators 10a-c based on the estimated remaining oil life of one or more of the generators 10a-c. The central controller 54 may control a switch array that selective couples multiple loads to the generator bus 11 in addition to circuit breakers 53a-c that selectively couple the generators 10a-c to the bus. The central controller 54 may calculate or receive the estimated remaining oil life for each of the generators 10a-c.

Consider an example in which each generator is rated 20 kW and each of three loads in 10 kW. With three loads connected and all three generators 10a-c closed to the bus, the generators 10a-c would operate at 50% of rated output. However, when one of the generators is approaching the end of the life of its current engine oil, the central controller 54 may disconnect that generator from the bus 11 and operate the other generators at 75% of the rated output.

Similarly, the central controller 54 may remove a load from the bus 11 based on oil life. For example, the central controller 54 may remove a generator when its oil life falls below a threshold, and when the remaining generators cannot adequately supply the load, a portion of the load may be removed. In response, to an estimated oil life being less than the threshold, the central controller 54 may generate a first switch command to disconnect a generator associated with the low oil life from the bus 11 and a second switch command to disconnect a portion of the load from the bus 11.

The central controller 54 may control the loads on generators 10a-c based on the estimated remaining oil life of the generators 10a-c in order to cause the generators 10a-c to reach the end of the oil life at near the same time. For example, when generator 10a has an estimated oil life that is below a threshold oil life, the central controller 54 may disconnect the generator 10a from the bus 11 if possible, which causes the load on generators 10b and 10c to increase and the oil life for generators 10b and 10c to decrease at a faster pace. When the oil life of generator 10b and/or 10c approaches or becomes equal to the oil life of generator 10a, the central controller 54 may reconnect the generator 10a to the bus. Through this technique, generators 10a-c will be due for an oil change at nearly the same time. Accordingly, service technician visits are minimized.

Figure 5:
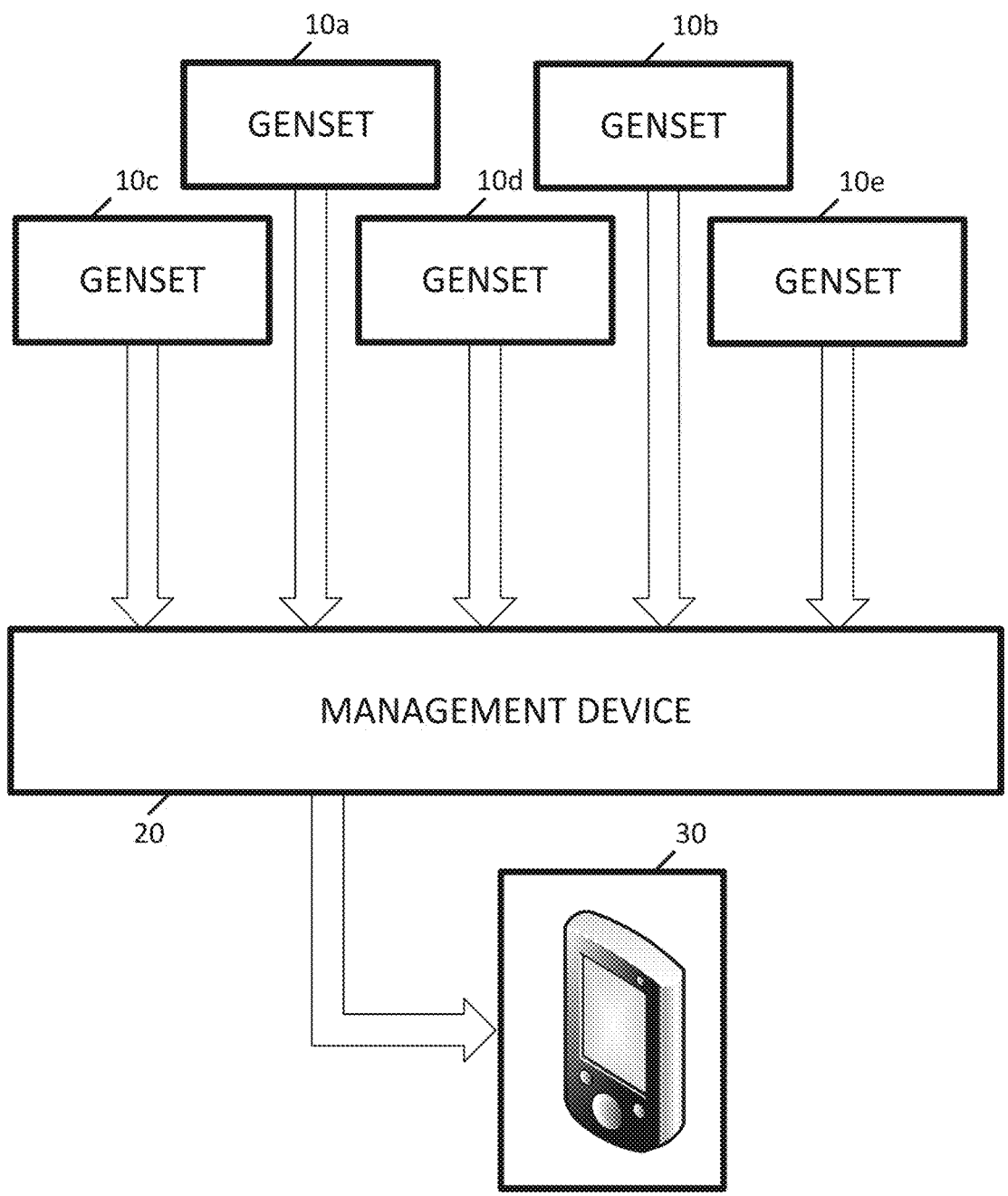
FIG. 5 illustrates an example network of generators including an external device associated with predicting oil life.

FIG. 5 illustrates an example network of generators 10a-e in communication with a management device 20 for predicting oil life. The generators 10a-e may be connected to the management device 20 using a network comprising any combination of a cellular telephone network, an 802.x network, a WiMax network, Ethernet, any of the protocols known as Bluetooth, or a wired network. The management device 20 may be in communication with one or more mobile device 30. The mobile device 30 may be a cellular phone, a smart phone, a personal digital assistance, a tablet computer, a personal computer, a laptop computer, or another device. The mobile device 30 and the management device 20 may be connected using the same network or a different network of any of the above technologies. Additional, different, or fewer components may be included.

The mobile device 30 may allow a user to monitor the operation of generators 10a-e. In one example, the mobile device 30 may display operating parameters (e.g., whether each generator is running, output levels, or other data). In addition or in the alternative, the mobile device 30 may display the estimated oil life for one or more of the generators 10a-e or a warning message when one of the generators 10a-e reach low oil life.

Figure 6:
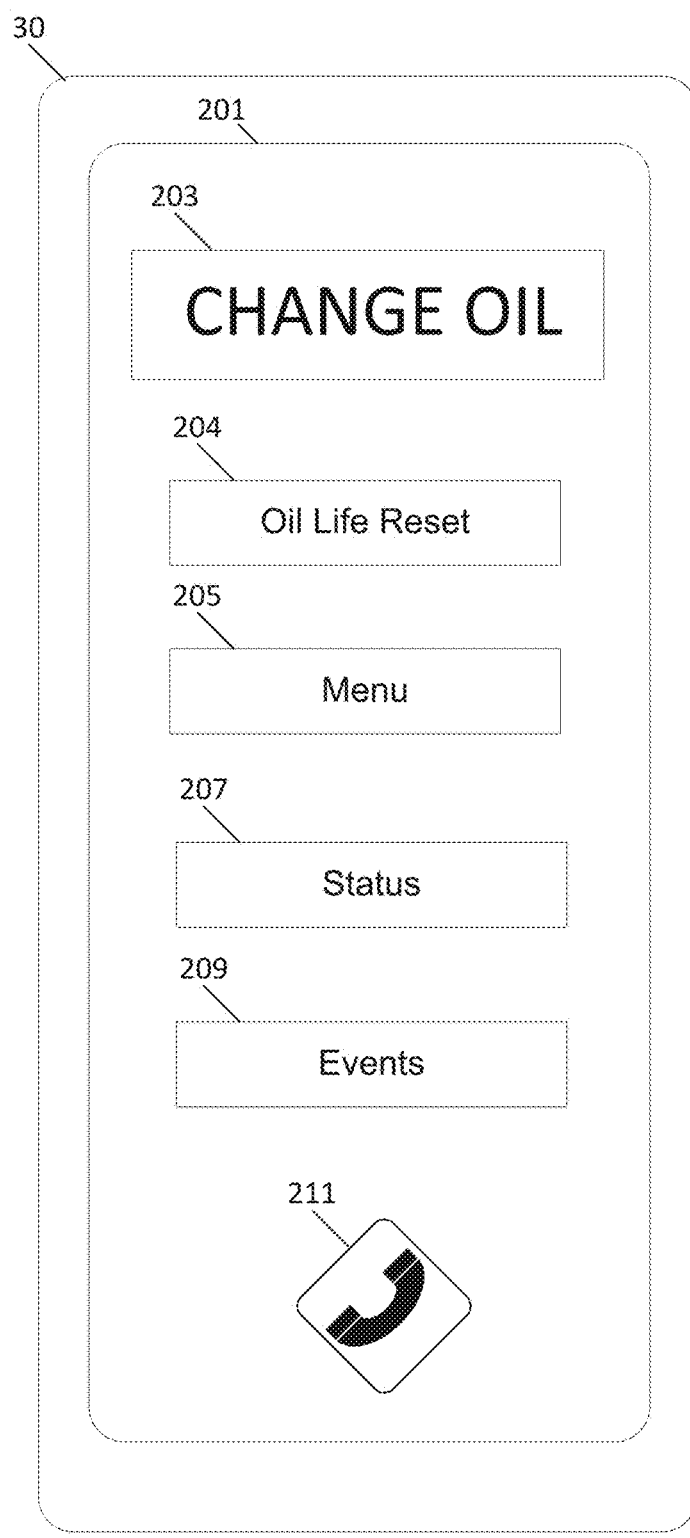
FIG. 6 illustrates an example user interface for the external device of FIG. 4.

FIG. 6 illustrates an example user interface 201 for the mobile device 30. The user interface 201 includes an oil change message 203, an oil life reset selection 204, a menu selection 205, a status selection 207, an events selection 209, and a communication button 211. Additional, different, or fewer selections or messages may be displayed by the user interface 201.

The oil change message 203 may be generated either by the mobile device 30, the management device 20, or generator controller 100 based on a comparison of the oil life estimation to a threshold. The oil change message 203 may include a percentage based on the difference between the oil life estimation and the threshold (e.g., less than 50% of the oil life is remaining, less than 10% of the oil life is remaining). The oil change message 203 may have other multiple forms or texts (e.g., "oil life ending in the next month," "oil life ending soon," or "oil change past due").

The oil life reset selection 204 may allow the user to reset the oil life calculation. In response to the oil life reset selection 204, the mobile device 30, the management device 20, or generator controller 100 may zero out the calculation in stage 39 in FIG. 2 or begin the calculation in stage 39 again (e.g., return the estimated oil life to a default value). In examples where the generator load or load factor are accumulated over time, the generator load or load factor may be reset to zero or another default value based on the oil life reset selection 204. The user may select the oil life reset selection 204 based on an oil change. In another example, the user may determine that an oil life message has been received in error and use the oil life reset selection 204 to repeat the oil life calculation. In another example, only a service technician has access to the oil life reset selection 204 based on a passcode.

The menu selection 205 may access a menu that allows the user to enter settings. The settings may include threshold values for the oil levels or settings for the generators a-e. The status selection 207 may initiate a request to the generator controller 100 to take a sample or reading of any of the sensors. The events selection 309 may cause the mobile application to present a history of usage. The history of usage may include time ranges when the generators were in operation. The history of usage may include dates of oil changes or a chart of the estimated oil life.

The communication button 211 may initiate a communication related to the mobile application. The communication may be an email, a phone call, a text message, or another communication. The communication may be sent to a service provider (e.g., oil change technician) for the generators or to the residence or business where the generators are installed.

Figure 7:
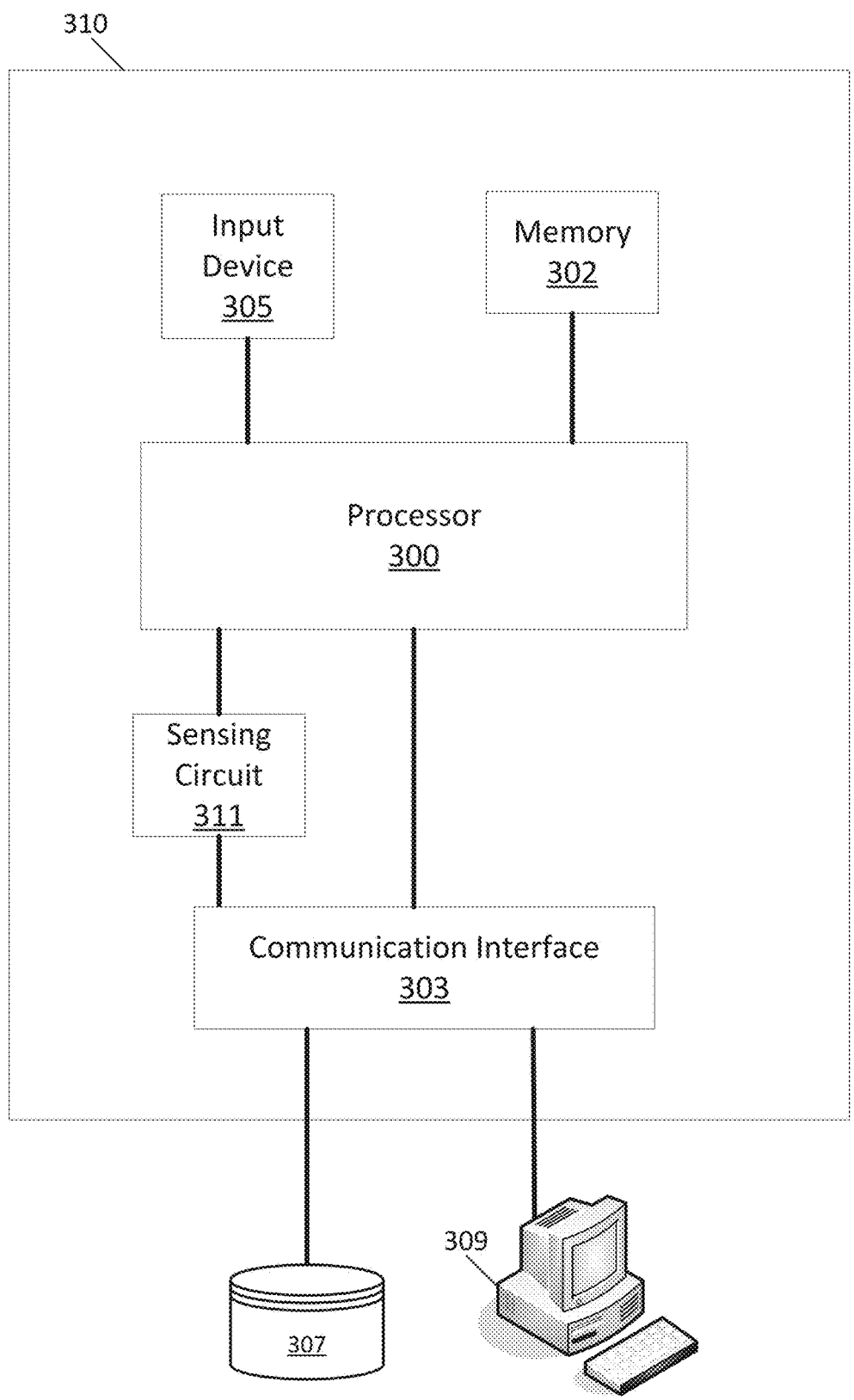
FIG. 7 illustrates an example controller for predicting oil life.
Figure 8:
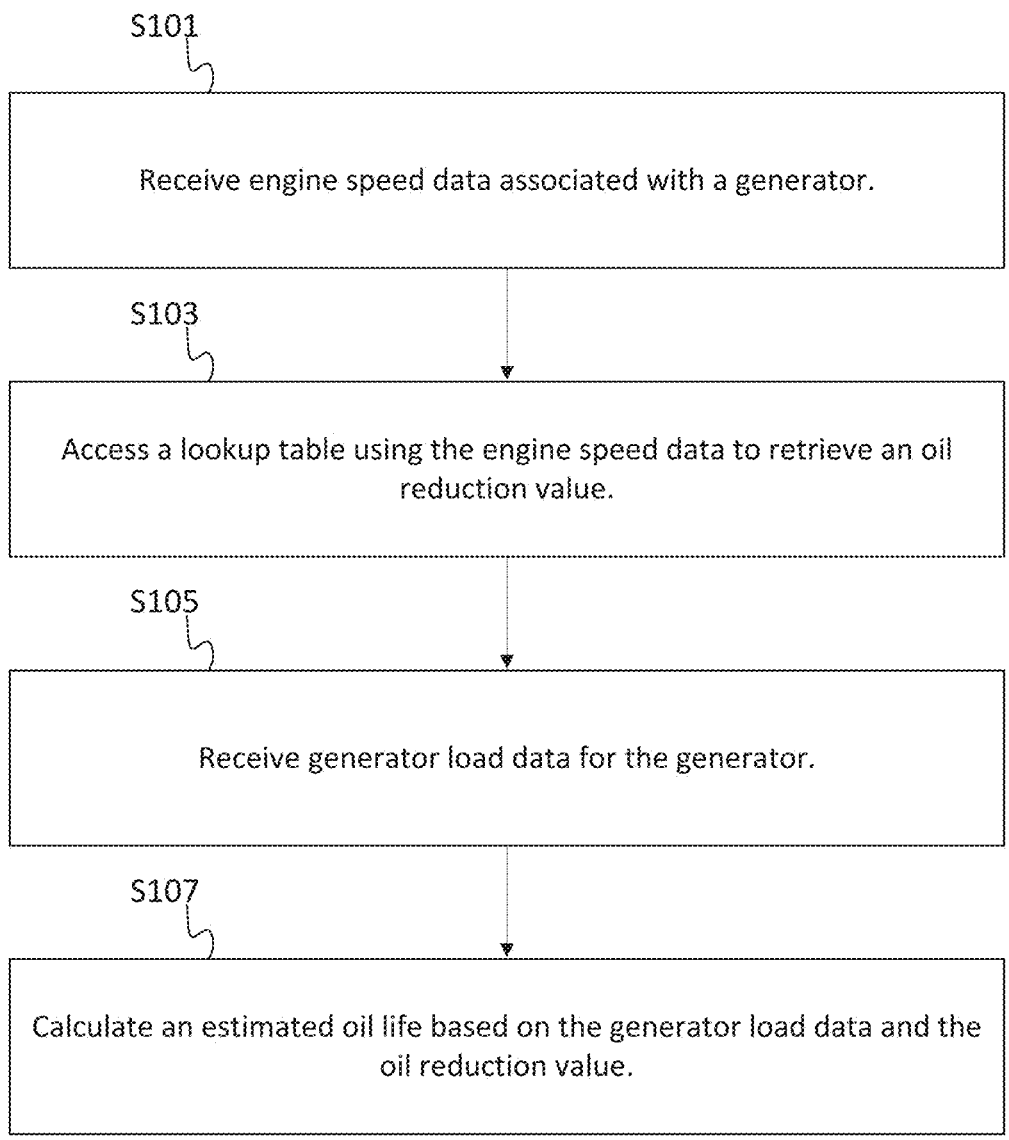
FIG. 8 illustrates example flowchart for predicting oil life.

FIG. 6 illustrates an example controller 310 for a system for predicating oil life. The controller 310 may correspond to one or more of generator controller 100, central control device 54, management device 20, mobile device 30 or another device. The controller 310 may include a processor 300, a memory 302, and a communication interface 303. The generator controller 10 may be connected to a workstation 309 or another external device (e.g., control panel) and/or a database 307. Optionally, the generator controller 10 may include an input device 305 and/or a sensing circuit 311. The sensing circuit 311 receives sensor measurements from the sensors above. Additional, different, or fewer components may be included. FIG. 7 illustrates an example controller for predicting oil life. The methods in FIG. 7 may, in some instances, be implemented as logic or software executable by a controller, such as controller 310. Additional, different, or fewer acts may be provided. The acts may be performed in the order shown or other orders. The acts may also be repeated.

The memory 302 may store current or past values for the oil life estimation. The oil life values may be indexed by an address or location of the generator and/or by generator type or model number. If the generator fails or power is lost, the oil life estimation is retained by memory 302. The memory 302 may also store values for the oil life thresholds described above.

At act S101, the communication interface 303 or the processor 300 receives engine speed data associated with an engine or an engine-generator. The engine speed data may be derived from a setting sent to the engine or based on sensor data measured from the engine.

At act S103, the processor 300 accesses a lookup table using the engine speed data to retrieve an oil reduction value. The lookup table may be stored at memory 302 or the database 307. The lookup table may associate engine models with oil reduction values that indicate how long engine oil typically lasts in those engines. The lookup table may associate generator models with oil reduction values that indicate how long engine oil typically last is the engines of those generators.

The processor 300 the communication interface 303 may also receive data indicative of an oil type. The oil type data may be entered by a user. The oil type data may be generated by a scanner or camera of the generator that reads a bar code or quick response (QR) code on the oil container. The scanner or camera may be mounted on the generator 10 or included on the mobile device 30. The oil type data may indicate synthetic, non-synthetic, an oil weight, an oil viscosity, or another value. The processor 300 may modify the oil reduction value based on the oil type input.

At act S105, the communication interface 303 or the processor 300 receives generator load data for the generator. The generator load data may include samples of the generator electrical output at predeterminate time intervals. The generator load data may be accumulated over a time range. The generator load data may be indicative of output power integrated over time. In any of these examples, the generator load data may include a time component and an output level component.

At act S106, the processor 300 calculates an estimated oil life based on the generator load data and the oil reduction value. High generator load also indicates high oil usage decreasing the amount of oil in the engine. This algorithm will provide the generator operator with an indication to 'change oil now' before enough oil is lost during operation causing the oil pressure to be too low thus causing engine damage. Under high loads the oil level can drop after less than (e.g., 60 hours) the oil's rated duration of operation (e.g., 100 hours).

The estimated oil life may be calculated by multiplying the time component and the output level component of the generator load data with the oil reduction value from the lookup table to calculate a scaled oil reduction value. The scaled oil reduction value may be subtracted from a default value to calculate the estimated oil life.

The processor 300 may include a general processor, digital signal processor, an application specific integrated circuit (ASIC), field programmable gate array (FPGA), analog circuit, digital circuit, combinations thereof, or other now known or later developed processor. The processor 300 may be a single device or combinations of devices, such as associated with a network, distributed processing, or cloud computing.

The memory 302 may be a volatile memory or a non-volatile memory. The memory 302 may include one or more of a read only memory (ROM), random access memory (RAM), a flash memory, an electronic erasable program read only memory (EEPROM), or other type of memory. The memory 302 may be removable from the network device, such as a secure digital (SD) memory card.

In addition to ingress ports and egress ports, the communication interface 303 may include any operable connection. An operable connection may be one in which signals, physical communications, and/or logical communications may be sent and/or received. An operable connection may include a physical interface, an electrical interface, and/or a data interface.

The communication interface 303 may be connected to a network. The network may include wired networks (e.g., Ethernet), wireless networks, or combinations thereof. The wireless network may be a cellular telephone network, an 802.11, 802.16, 802.20, or WiMax network. Further, the network may be a public network, such as the Internet, a private network, such as an intranet, or combinations thereof, and may utilize a variety of networking protocols now available or later developed including, but not limited to TCP/IP based networking protocols.

While the computer-readable medium (e.g., memory 302 or database 307) is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored. The computer-readable medium may be non-transitory, which includes all tangible computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

As used in this application, the term 'circuitry' or 'circuit' refers to all of the following: (a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a micropro-cessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in server, a cellular network device, or other network device.

Processors suitable for the execution of a computer program include, by way of example, both general and special purpose microprocessors, and anyone or more processors of any kind of digital computer. Generally, a processor may receive instructions and data from a read only memory or a random access memory or both. The essential elements of a computer are a processor for performing instructions and one or more memory devices for storing instructions and data. Generally, a computer may also include, or be operatively coupled to receive data from or transfer data to, or both, one or more mass storage devices for storing data, e.g., magnetic, magneto optical disks, or optical disks. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope and spirit of the following claims and equivalents thereto are claimed as the invention.

I claim:

1. A method of operating a generator, the method comprising:
   receiving generator data for operation of the generator;
   receiving engine data for operation of an engine coupled to the generator;
   determining a generator command for the operation of the generator, the generator command based on the generator data or the engine data;
   calculating an estimated oil life from the generator command; and
   providing an oil life message in response to the calculated estimated oil life for an indication of accurate oil life.

2. The method of claim 1, further comprising:
   generating an oil life message based on the estimated oil life.

3. The method of claim 1, wherein the generator command includes a start command to initiate the operation of the generator or an adjustment command to adjust the operation of the generator.

4. The method of claim 1, further comprising:
   generating a generator status message for an operating state of the generator.

5. The method of claim 1, wherein the engine data includes engine speed or oil temperature.

6. The method of claim 1, further comprising:
   receiving a reset signal for the estimated oil life; and
   resetting the estimated oil life to a default value based on the reset signal.

7. The method of claim 1, further comprising:
   setting a field current for the generator according to the generator command.

8. The method of claim 1, wherein the generator command includes an output level for the generator.

9. An apparatus for operating a generator comprising:
   a memory configured to store generator data for operation of the generator and engine data for operation of an engine coupled to the generator; and
   a processor configured to determine a generator command to initiate or adjust the operation of the generator, the processor further configured to calculate an estimated oil life based on the generator command and provide an oil life message in response to the calculated estimated oil life for an indication of accurate oil life.

10. The apparatus of claim 9, wherein the processor is configured to perform a comparison of the estimated oil life to a threshold value and generate a warning message based on the comparison.

11. A method of operating a generator, the method comprising:
    receiving engine speed data associated with the generator;
    accessing a lookup table according to a type of the generator using the engine speed data to retrieve an oil reduction value;
    receiving generator load data for the generator;
    calculating an estimated oil life based on the generator load data and the oil reduction value; and
    providing an oil life message in response to the calculated estimated oil life for an indication of accurate oil life.

12. The method of claim 11, wherein the generator load data includes a time component and an output level component.

13. The method of claim 12, further comprising:
    multiplying the time component, the output level component and the oil reduction value to calculate a scaled oil reduction value; and
    subtracting the scaled oil reduction value from a default value to calculate the estimated oil life.

14. The method of claim 11, further comprising:
    comparing the estimated oil life to a maximum value; and
    setting the estimated oil life to the maximum value when the estimated oil life exceeds the maximum value.

15. The method of claim 11, further comprising:
    comparing the estimated oil life to a warning threshold value; and
    generating a warning message with the estimated oil life exceeds the warning threshold value.

16. The method of claim 11, further comprising:
    receiving an oil type input; and
    modifying the oil reduction value based on the oil type input.

17. The method of claim 16, wherein the oil type input is received from a scanner.

18. The method of claim 11, wherein the lookup table includes different oil reduction values for different models of generators.

* * * * *